United States Patent
Yamaguchi

(10) Patent No.: US 9,897,580 B2
(45) Date of Patent: Feb. 20, 2018

(54) MULTI-DIMENSIONAL CHROMATOGRAPH SYSTEM

(75) Inventor: Shinichi Yamaguchi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 652 days.

(21) Appl. No.: 14/379,451

(22) PCT Filed: Feb. 23, 2012

(86) PCT No.: PCT/JP2012/054364
§ 371 (c)(1),
(2), (4) Date: Aug. 18, 2014

(87) PCT Pub. No.: WO2013/125001
PCT Pub. Date: Aug. 29, 2013

(65) Prior Publication Data
US 2015/0034812 A1    Feb. 5, 2015

(51) Int. Cl.
*G01N 30/86* (2006.01)
*G01N 30/72* (2006.01)
*G01N 30/46* (2006.01)
*B01D 15/18* (2006.01)
*B01D 15/42* (2006.01)

(52) U.S. Cl.
CPC ..... *G01N 30/7233* (2013.01); *B01D 15/1878* (2013.01); *B01D 15/424* (2013.01); *G01N 30/463* (2013.01); *G01N 30/8651* (2013.01); *G01N 30/8655* (2013.01)

(58) Field of Classification Search
CPC .... G01N 30/02; G01N 30/86; G01N 30/8651; G01N 30/8655; G01N 30/8675; G01N 30/8696
See application file for complete search history.

(56) References Cited

U.S. PATENT DOCUMENTS

2007/0005254 A1    1/2007 Nilsson et al.

FOREIGN PATENT DOCUMENTS

| JP | 2011-122822 A | 6/2011 |
|---|---|---|
| JP | 2012-2544 A | 1/2012 |

OTHER PUBLICATIONS

Malerod et al, Anal. Methods, Issue 2, pp. 110-122 (2010).*
Chinese Office Action issued May 4, 2015 in corresponding Chinese Patent Application No. 201280070557.1.
(Continued)

*Primary Examiner* — Jan Ludlow
(74) *Attorney, Agent, or Firm* — Sughrue Mion, PLLC

(57) ABSTRACT

In a two-dimensional LC system configured to introduce components trapped in a trap column during a fractionation period T into a second-dimension column, separate components, and then detect the components using a mass spectrometer, a data collection unit receives a signal which indicates timing to delimit the fractionation period T, determines the first data item in the fractionation period T, adds measurement start point identification information to the first data item, and stores all the data in a data storage unit. A two-dimensional chromatogram creation unit recognizes the first data item in each fractionation period T from the read data, and create a two-dimensional chromatogram by aligning data so that the first data items will be aligned at the top along an abscissa.

5 Claims, 4 Drawing Sheets

(56) References Cited

OTHER PUBLICATIONS

Communication dated Dec. 7, 2015 from the State Intellectual Property Office of the P.R.C. in counterpart application No. 201280070557.1.
European Search Report dated Dec. 15, 2014 in European Patent Application No. 12869529.3.
International Search Report for PCT/JP2012/054364 dated May 22, 2012.

* cited by examiner

MULTI-DIMENSIONAL CHROMATOGRAPH SYSTEM

CROSS REFERENCE TO RELATED APPLICATIONS

This application is a National Stage of International Application No. PCT/JP2012/054364 filed Feb. 23, 2012, the contents of which are incorporated herein by reference in their entirety.

TECHNICAL FIELD

The present invention relates to a multi-dimensional chromatograph system such as a multi-dimensional liquid chromatograph (multi-dimensional LC) and multi-dimensional gas chromatograph (multi-dimensional GC), and in particular, to a multi-dimensional chromatograph system suitable for use when a mass spectrometer is used as a detector.

BACKGROUND ART

The liquid chromatograph (LC) has various separation modes including normal phase mode, reversed phase mode, absorption mode, ion exchange mode, and size exclusion mode, and generally an appropriate separation mode is used according to the type of target sample or other factors. However, for a complicated sample such as an enzyme digesting protein mixture, one-dimensional separation using a single separation mode sometimes may not provide sufficient peak separation. As an advanced analysis technique for use in such a case, a technique called multi-dimensional LC is known which uses a combination of two or more separation modes not affected by each other (refer to Patent Literature 1).

In a typical two-dimensional LC, a flow of mobile phase carrying a liquid sample is introduced into a first-dimension column, components in the liquid sample are separated in the first-dimension column, the sample eluted from the first-dimension column during a predetermined fractionation period T is passed through a trap column, and thereby components of the sample are trapped in the trap column. Next, another mobile phase is passed through the trap column, the components trapped as such are eluted in a narrow time band and introduced into a second-dimension column, and components are further separated in the second-dimension column. Then, an eluate from the second-dimension column is introduced into a detector such as a mass spectrometer or UV/visible spectroscopic detector to chronologically detect the components in the eluate. Normally plural trap columns are prepared, and the trap columns for trapping components are switched from one to another at every fractionation period T, allowing the components in the eluate from the first-dimension column to be trapped without omission and sent to the second-dimension column.

Generally, the two-dimensional LC uses columns having different separation characteristics for the first-dimension column and second-dimension column, and various components in the sample to be analyzed are separated properly by the two column stages differing in the separation characteristics. FIG. 5 is an example of a chromatogram created based on the detection data obtained by a two-dimensional LC. In the chromatogram, narrow peaks appearing in sequence along the direction of time (along the abscissa) are components separated by the second-dimension column.

As can be seen from FIG. 5, in the two-dimensional LC, rough separation is performed in the first-dimension column and finer separation is performed in the second-dimension column. Therefore, if a two-dimensional chromatogram is created with retention time in the first-dimension column being taken as the abscissa and retention time in the second-dimension column being taken as the ordinate and with signal strength being represented by a color scale, gray scale, or other methods, a state of two-dimensional separation by two independent columns can be expressed adequately.

When the time (the fractionation period T) allotted to trap components in one trap column is always constant and the time interval at which a detection signal is obtained by a detector is also constant, the number of detection data items obtained within the fractionation period T is always constant. In this case, as shown in FIG. 6, if a sequence of detection data obtained chronologically during the fractionation period T are arranged along the direction of retention time (along the ordinate) of the second-dimension column of a two-dimensional chromatogram, and the sequence of detection data is arranged so that the sequence is shifted one by one in the direction of retention time (along the abscissa) of the first-dimension column at every interval of the fractionation period T, a good two-dimensional chromatogram can be created. However, depending on the type of detector or depending on detection conditions, the time interval at which the detection signals are obtained may not be constant.

For example, when a mass spectrometer is used as a detector, scan measurements are conducted in the mass spectrometer and the signal strengths of all ions are totaled for each scan measurement as detection data at a given measurement time point. Tandem quadrupole mass spectrometers capable of MS/MS analysis are sometimes used as a detector, but some tandem quadrupole mass spectrometers have an auto $MS^n$ function in which a precursor ion is automatically selected from a mass spectrum obtained by a scan measurement and then promptly a subsequent MS/MS analysis is perform (Refer to Patent Literature 2). On such a tandem quadrupole mass spectrometer, when auto $MS^n$ analysis is performed in the intervals between repeated scan measurements, the scan measurements are not repeated strictly at constant intervals. The reason is as follows. When any ion to be subjected to subsequent MS/MS analysis is found as a result of a scan measurement, MS/MS analysis is then performed, causing a delay in the start of next scan measurement accordingly. But when no ion to be subjected to MS/MS analysis is found as a result of a scan measurement, the next scan measurement is performed immediately. In another case, when plural ions to be subjected to MS/MS analysis are found, MS/MS analysis is performed using each of the ions as a precursor ion, further delaying the start of the next scan measurement and consequently extending the time interval at which detection data is obtained.

When the number of detection data items obtained within the fractionation period T is not constant due to factors such as described above, problems such as described below arise in creating a two-dimensional chromatogram.

Suppose, for example, the fractionation period T is set to 2 [min] and the repetition frequency of scan measurements is approximately 2.5 [Hz]. The repetition frequency is "approximately" 2.5 [Hz] because the repetition cycle becomes longer, as described above, than that at the basic repetition frequency of 2.5 [Hz] if MS/MS analysis is performed in real time by the automatic $MS^n$ function. Therefore, when no MS/MS analysis is performed between scan measurements, the number of scan measurements performed within the fractionation period T, i.e., the number of scans, is 120 [sec]×2.5 [Hz]=300. However, when MS/MS analysis is performed in an interval between scan measurements, the number of scans may be, for example, 298, which is less than 300. Also, as a result of a scan measurement, when a large number of precursor ions are selected and MS/MS analyses are performed corresponding number of times, scan measurement intervals are extended further, resulting in a still smaller number of scans. That is, during data collection by two-dimensional LC, even if the fractionation period T is constant, the number of detection data items obtained within the fractionation period T is indeterminate.

On the other hand, in creating a two-dimensional chromatogram, a predetermined number of detection data items obtained with the passage of time are arranged along the ordinate of a graph. For example, in the above example, the standard number of scans within the fractionation period T is 300. If a shift by the fractionation period T along the abscissa is repeated every 300 detection data items arranged along the ordinate, a two-dimensional chromatogram can be created. An example of a two-dimensional chromatogram created in this way is shown in FIG. 8. The ordinate represents the number of scans, which is equivalent to the number of detection data items. However, as described above, when the number of detection data items obtained within the fractionation period T is, for example, 298 or 297 rather than 300, the data lined up vertically on the two-dimensional chromatogram shown in FIG. 8 does not correctly reflects the state of separation in the second-dimension column. That is, some data items on the upper end side of the vertical line belong to the data in the next fractionation period while some data items on the lower end side of the vertical line are missing.

FIG. 7 is a two-dimensional chromatogram created by arranging 298 detection data items along the ordinate using the same detection data as the two-dimensional chromatogram shown in FIG. 8. Comparing FIG. 7 and FIG. 8, it is apparent that they show quite different states of two-dimensional separation. It can be seen that the peak located in the lower part (the part of shorter retention time in the second-dimension column) in FIG. 7 is relocated in the upper part in FIG. 8. When two such two-dimensional chromatograms are presented, it is difficult for an analyst to determine which of the two reflects a more appropriate state of separation. In any case, with the conventional technique for creating a two-dimensional chromatogram, when the number of data items obtained within the fractionation period T is indeterminate, an inappropriate image which does not correctly reflect the state of separation in an actual column can be obtained.

CITATION LIST

Patent Literature

[Patent Literature 1] JP 2011-122822 A
[Patent Literature 2] JP 2012-002544 A

SUMMARY OF INVENTION

Technical Problem

The present invention has been made in view of the above problems and is addressed to an object to provide a multi-dimensional chromatograph system which can create a multi-dimensional chromatogram capable of expressing a state of multi-dimensional separation correctly even when the time intervals at which detection data is obtained are indeterminate or the number of detection data items obtained within a fixed fractionation period is indeterminate.

Solution to Problem

To solve the aforementioned problems, the present invention provides a multi-dimensional chromatograph system comprising: an (n−1)th-dimension column (where n is an integer equal to or larger than 2) configured to chronologically separate a plurality of components contained in a sample; a holding unit configured to hold components of the sample, the components being obtained from the (n−1)th-dimension column within a predetermined time period; an nth-dimension column configured to further chronologically separate components of the sample held by the holding unit; and a detection unit configured to detect the components of the sample in sequence, the components being obtained from the nth-dimension column, wherein the components of the sample obtained from the (n−1)th-dimension column are fractionated at every predetermined time period and held by the holding unit, and an operation in which the components held by the holding unit are separated in the nth-dimension column and detected is performed repeatedly, the multi-dimensional chromatograph system further comprising:

a) data collection means for collecting data items obtained in sequence by the detection unit and recording the data items by adding information to the data items or by associating the information with the data items, the information being capable of identifying data delimitation corresponding to a fractionation of the sample at every predetermined time period; and b) multi-dimensional chromatogram creation means for determining, based on the information capable of identification, a first data item obtained in relation to the predetermined time period among the data items collected by the data collection means and creating a graph by aligning the data items so as to arrange the first data items of the data items along an axis in a direction of one dimension.

In the multi-dimensional chromatograph system according to the present invention, n is typically 2. Also, in the present invention, a chromatograph is generally a liquid chromatograph (LC) or gas chromatograph (GC).

In the multi-dimensional chromatograph system according to the present invention, although the type of detector is not particularly limited, the present invention is particularly useful when a detector is used with which the number of data items obtained in relation to a predetermined time period is not constant because the time interval at which detection data is acquired is not constant. Examples of such a detector include a tandem quadrupole mass spectrometer and ion trap time-of-flight mass spectrometer equipped with an auto $MS^n$ function to automatically determine based on a mass spectrum whether there is any ion to be subjected to $MS^n$ analysis and perform $MS^n$ analysis in real time if there is any ion to be subjected to $MS^n$ analysis, in intervals between repetitions of scan measurements or time-of-flight analyses capable of producing a mass spectrum.

In the multi-dimensional chromatograph system according to the present invention, the data collection means and the multi-dimensional chromatogram creation means can adopt any of various configurations.

In one aspect of the multi-dimensional chromatograph system according to the present invention, the data collection means may be configured to record the data obtained in relation to the predetermined time period by adding an identifier to one of the first item and a last item of the data; and the multi-dimensional chromatogram creation means may be configured to determine the first item of the data obtained in relation to the predetermined time period based on the identifier.

Also, in another aspect of the multi-dimensional chromatograph system according to the present invention, the data collection means may be configured to count and record the number of data items obtained in relation to the predetermined time period at every predetermined time period starting from the beginning of measurement; and the multi-dimensional chromatogram creation means may be configured to determine the first item of the data obtained in relation to the predetermined time period based on the count.

Also, in another aspect of the multi-dimensional chromatograph system according to the present invention, the data collection means may be configured to record a serial number given to one of the first item and a last item of the data obtained in relation to the predetermined time period, the serial numbers being given according to chronological order of data starting from the beginning of measurement or from a predetermined time point; and the multi-dimensional chromatogram creation means may be configured to determine the first item of the data obtained in relation to the predetermined time period based on the recorded number.

Also, in still another aspect of the multi-dimensional chromatograph system according to the present invention, the data collection means may be configured to record acquisition time of each data item counting from the beginning of measurement or from a predetermined time point; and the multi-dimensional chromatogram creation means may be configured to determine the first item of the data obtained in relation to the predetermined time period, based on the recorded acquisition time.

That is, in any of the above aspects, the multi-dimensional chromatogram creation means can find the first item of the data obtained in relation to the predetermined time period based on additional information recorded together with the data or by being associated with the data. This makes it possible to create a multi-dimensional chromatogram in which regardless of the number of data items acquired in relation to the predetermined time period, i.e., fractionation period, multiple items of data obtained in relation to one fractionation period will be arranged in a line along a direction of one dimension which represents separation characteristics of the nth-dimension column, in other words, data obtained in relation to a different fractionation period will not be mixed in multiple items of the data arranged in a line along the direction of one dimension which represents the separation characteristics of the nth-dimension column.

It should be noted that when the number of data items obtained in relation to each fractionation period is not constant, the positions of the last data items are not aligned in case the first data items are aligned along one dimension, for example, along the abscissa. In such a case, the missing portion on the graph may be filled in with dummy data points or a display region for each set of data may be enlarged or shrinked appropriately so that the last data items will be aligned. Generally, when a scan interval is elongated and the data points during a fractionation period are scarce, it is better not to fill the period with dummy data but to evenly distribute the data points in the display region during the corresponding time period in order to obtain a less distorted image points. Furthermore, if measuring time information is given to each scan and a two-dimensional image is formed by arranging data based on the measuring time information, the state of two-dimensional separation can be reproduced more correctly.

Advantageous Effects of Invention

The multi-dimensional chromatograph system according to the present invention provides a multi-dimensional chromatogram which can express a state of multi-dimensional component separation adequately even when the time intervals at which detection data is obtained by the detector are indeterminate or the number of detection data items obtained within a fixed time period is indeterminate. This makes it easy to properly understand properties of each component, for example, when a large number of components are contained in a sample. Also, it becomes easy to compare components among plural samples which contain the components.

DESCRIPTION OF EMBODIMENT

Figure 1:
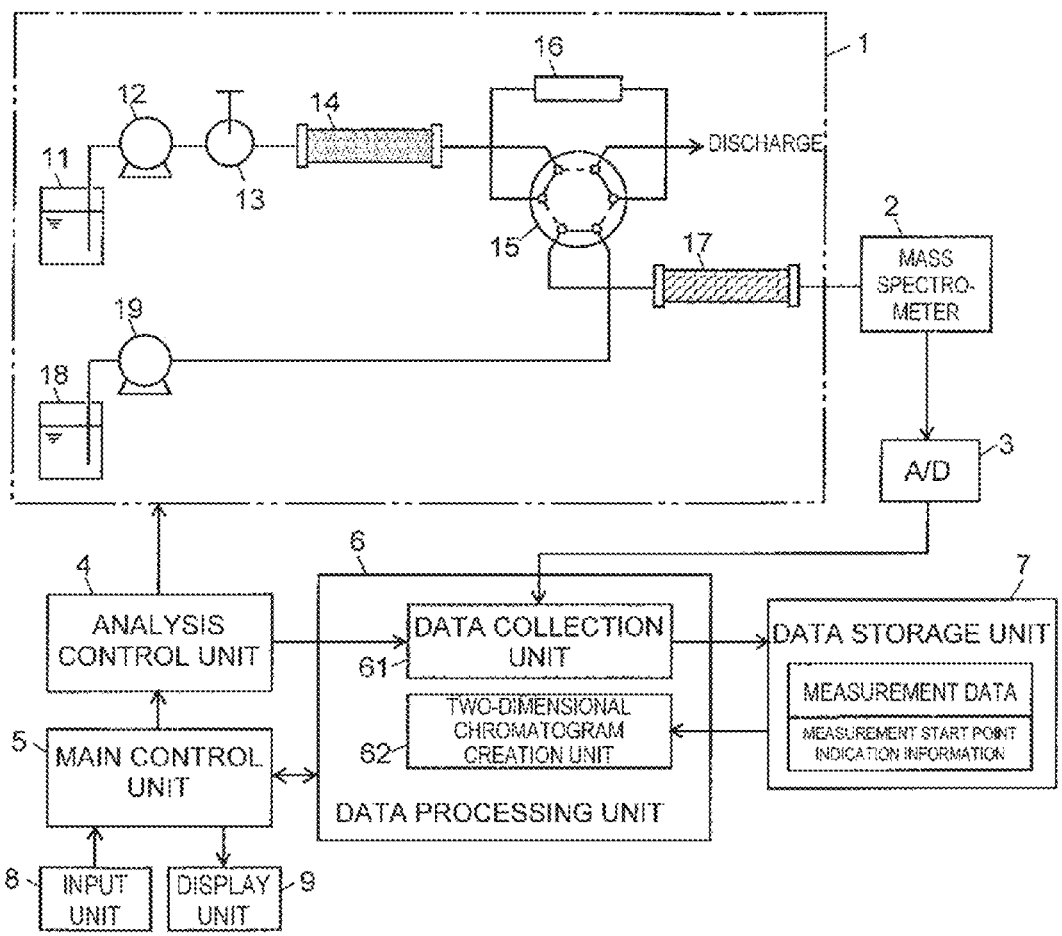
FIG. 1 is a schematic configuration diagram of a two-dimensional LC system according to an embodiment of the present invention.

A two-dimensional LC system, which is an embodiment of the present invention, will be described below with reference to the accompanying drawings. FIG. 1 is a schematic configuration diagram of a two-dimensional LC system according to the present embodiment.

In the two-dimensional LC system according to the present embodiment, a separation unit 1 includes a first mobile phase container 11, a first pump 12, an injector 13, a first-dimension column (which corresponds to the (n−1)th-dimension column according to the present invention) 14, a 2-position 6-ports change-over valve 15, a trap column (which corresponds to the holding unit according to the present invention) 16, a second-dimension column (which corresponds to the nth-dimension column according to the present invention) 17, a second mobile phase container 18, and a second pump 19. The first-dimension column 14 and second-dimension column 17 have different separation characteristics. It should be noted that although actually means of selectively draining cleaning fluids used to wash the inside of the trap column 16 and other flow channels is necessary in order to avoid contamination, such means departs from the scope of the present invention, and is thus omitted. Also, although a configuration equipped with plural trap columns may be adopted as described below, a configuration equipped with a single trap column is shown here for simplicity of explanation. Furthermore, a loop tube or the like may be used instead of the trap column.

An eluate from the second-dimension column 17 is introduced into a mass spectrometer (which corresponds to the detector according to the present invention) 2, the mass spectrometer 2 detects various components in the eluate and outputs detection signals of strengths corresponding to the amounts of components. The mass spectrometer 2 is, for example, a tandem quadrupole mass spectrometer, is able to perform scan measurements for detecting ions originating from sample components while repeatedly scanning mass-to-charge ratios over a specified mass-to-charge ratio range, and is equipped with an auto $MS^n$ function to perform MS/MS analysis in real time using the ions extracted based on scan measurement results as precursor ions.

The detection signals of the mass spectrometer 2 are converted into digital data by an A/D converter 3 and inputted to a data processing unit 6. The data processing unit 6 includes functional blocks such as a data collection unit 61 and two-dimensional chromatogram creation unit 62. The data collection unit 61 stores data inputted when measurements are performed, in a data storage unit 7. Also, the two-dimensional chromatogram creation unit 62 creates a two-dimensional chromatogram using the data stored in the data storage unit 7.

The separation unit 1 and mass spectrometer 2 are controlled by an analysis control unit 4, a main control unit 5 configured to exert overall control over the entire system including the analysis control unit 4 is connected with an input unit 8 and display unit 9 serving as user interfaces. At least part of the functions of the main control unit 5, analysis control unit 4, and data processing unit 6 can be implemented by using a personal computer as a hardware resource and executing special-purpose control/processing software installed on the personal computer in advance.

The two-dimensional LC system according to the present embodiment performs measurements of a target sample and collects measurement data according to the procedures described below.

That is, when the change-over valve 15 in the connection mode indicated by solid lines in FIG. 1, a mobile phase A drawn from the mobile phase container 11 by the first pump 12 is discharged through the injector 13, first-dimension column 14, and trap column 16. When a target sample is injected from the injector 13 into a mobile phase A with predetermined timing, the target sample is introduced into the first-dimension column 14, being carried by the flow of the mobile phase A. Then, while the target sample is passing through the first-dimension column 14, contained components are separated. When an eluate coming out of the first-dimension column 14 and containing the separated components passes through the trap column 16, various components in the eluate are trapped in the trap column 16.

When the components in the eluate are trapped in the trap column 16 for a predetermined time (fractionation period) T set in advance, the change-over valve 15 is switched to the connection mode indicated by dotted lines in FIG. 1. This time, a mobile phase B drawn from the second mobile phase container 18 by the second pump 19 is sent to the trap column 16. The components trapped earlier in the trap column 16 is eluted by the mobile phase B and introduced into the second-dimension column 17. Eluting power of the mobile phase B is high, and thus the elution of the components trapped earlier in the trap column 16 is finished in a short time.

After various components trapped during one fractionation period T are introduced into the second-dimension column 17 by the flow of the mobile phase B, the change-over valve 15 switches back to the connection mode indicated by the solid lines in FIG. 1, and the mobile phase B supplied at a constant flow rate by the second pump 19 is fed continuously into the second-dimension column 17. The various components introduced into the second-dimension column 17 are separated more finely while passing through the column 17 and the various components originally contained in the target sample are eluted from the second-dimension column 17 by being shifted in time.

It should be noted that in a configuration which uses one trap column 16 as shown in FIG. 1, after the components trapped earlier in the trap column 16 are carried away by the mobile phase B, an operation can be performed in which the eluate containing the components separated by the first-dimension column 14 is passed through the trap column 16 again and the components in the eluate are trapped in the trap column 16. However, with this configuration, during a period in which the components trapped in the trap column 16 are introduced into the second-dimension column 17 by the mobile phase B, the components in the eluate sent from the first-dimension column 14 cannot be held.

Thus, the configuration shown in FIG. 1 can be changed to a configuration equipped with plural trap columns in a switchable fashion. With such a configuration, if an operation is performed in which trap columns adapted to pass the eluate coming from the first-dimension column 14 are switched in sequence and while the eluate from the first-dimension column 14 is being passed through one trap column, the components eluted from another trap column are introduced into the second-dimension column 17, all the components contained in the target sample can be detected without omission.

In simple terms, in the separation unit 1, the components eluted from the first-dimension column 14 during the fractionation period T are introduced into the second-dimension column 17 by temporally compressing the components and secondary separation is performed at high resolution when the components pass through the second-dimension column 17. The eluate containing the components thus separated two-dimensionally is introduced into the mass spectrometer 2. In the mass spectrometer 2, scan measurements in a predetermined mass-to-charge ratio range are repeated, and in some cases, MS/MS analysis is performed automatically between a scan measurement and next scan measurement using, as precursor ions, the ions selected based on a mass spectrum obtained by scan measurements.

Next, characteristic data collection operation performed mainly by the data processing unit 6 when the measurements described above are conducted in the two-dimensional LC system according to the present embodiment will be described with reference to FIG. 2. Here, attention will be focused only on collection of the mass spectrum data obtained by scan measurement and the collection of data obtained by MS/MS analysis performed in the intervals between scan measurements will be ignored. Also, the mass spectrum data made up of multiple items of data (or a series of profile data) obtained by one scan measurement will be denoted by D* (where * is 1, 2, . . . ).

The fractionation period T can be set by a user via the input unit 8, and it is assumed here that the fractionation period T during measurement of one sample is constant, and is T=2[min]. On the other hand, the repetition period of scan measurements can also be specified by the user via the input unit 8, and the specified repetition period is strictly the shortest period and the repetition period becomes longer with increases in the running time of the MS/MS analysis performed as described above in the intervals between scan measurements. It is assumed here that the shortest repetition period of scan measurements is 2.5[Hz].

When the fractionation period is T=2[min] as described above, if the repetition period of scan measurements is 2.5 [Hz], scan measurements are repeated 300 times during the fractionation period T. Since mass spectrum data D* is inputted to the data collection unit 61 after each scan measurement, the number of items of mass spectrum data inputted to the data collection unit 61 during the fractionation period T is 300. With respect to the data inputted chronologically, delimitation between fractionation periods T depends on switching control timing of the change-over valve 15 by the analysis control unit 4. The data collection unit 61 receives a signal which indicates timing to delimit the fractionation period T from the analysis control unit 4 and determines the first data item in the fractionation period T. If the number of scan measurements conducted during the fractionation period T is 300 as described above, since the number of items of mass spectrum data obtained during the fractionation period T is 300, it is determined that the first data items in the fractionation periods T are D1, D301, D601, . . . as shown in Part (a) of FIG. 2.

The data collection unit 61 sequentially stores data received from the A/D converter 3 in a storage area of the data storage unit 7, and in so doing, adds measurement start point indication information (e.g., a flag) to the first data item in the fractionation period T determined in the manner described above, and stores the information with associating the information with the data. A storage area for use to store the measurement start point indication information may be provided separately from the data storage area, but when data is stored byte by byte (e.g., in 2-byte or 3-byte groups) and there is any free (unused) bit in a byte, the free bit can be used to record the measurement start point indication information.

Figure 2:
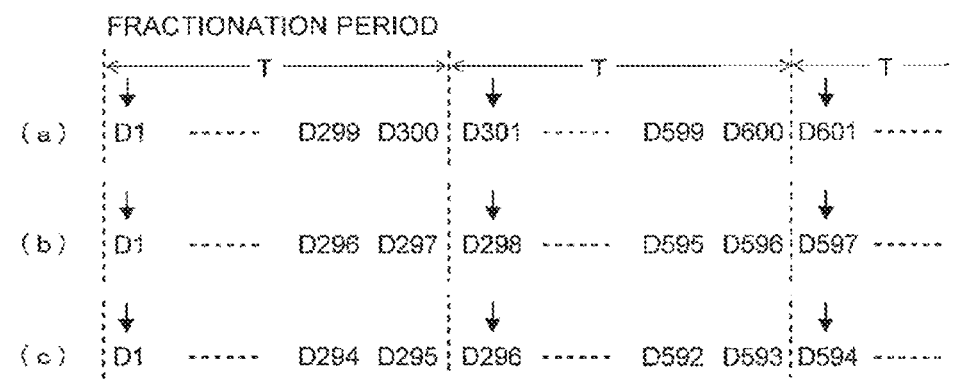
FIG. 2 is an explanatory diagram of data collection operation performed by the two-dimensional LC system according to the present embodiment.
Figure 3A:
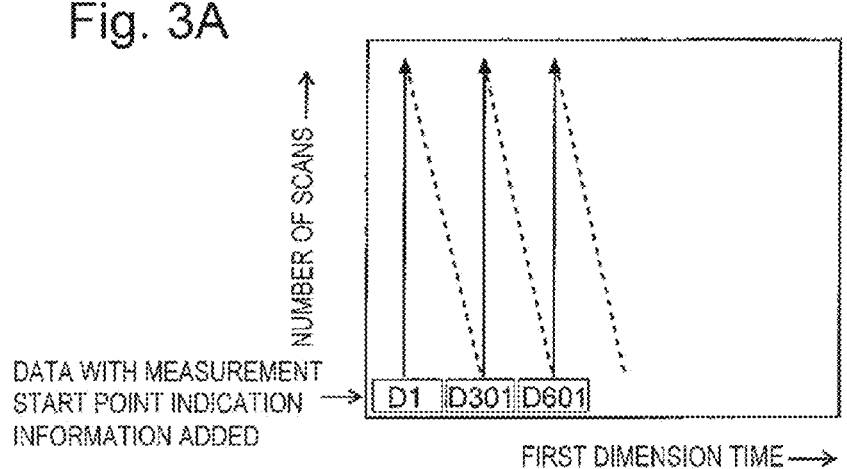
FIG. 3A, FIG. 3B, and FIG. 3C are explanatory diagrams of two-dimensional chromatogram creation operation performed by the two-dimensional LC system according to the present embodiment.
Figure 3B:
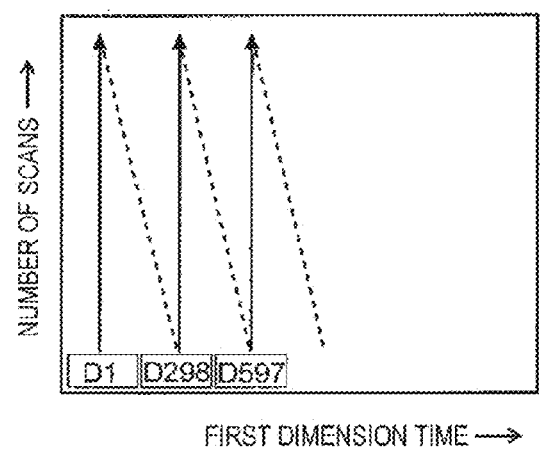
Figure 3C:
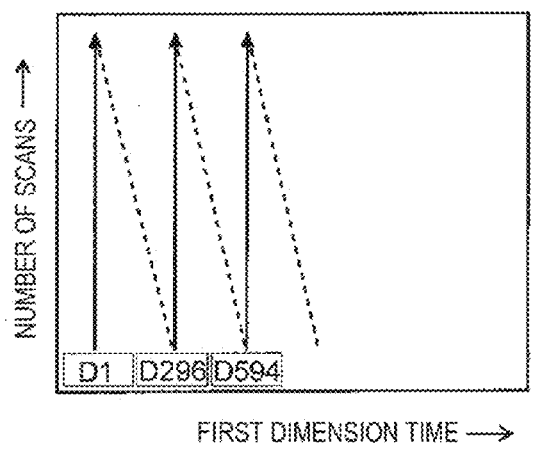

In the example in Part (a) of FIG. 2, the measurement start point indication information is added to D1, D301, D601, . . . marked with downward-pointing arrows. As described above, when MS/MS analysis is performed in intervals between scan measurements, the number of scan measurements conducted during the fractionation period T may become less than 300. In that case, the number of items of mass spectrum data obtained during the fractionation period T becomes less than 300. In the example of FIG. 3B, the number of items of mass spectrum data obtained during the fractionation period T is 297, 299, . . . . In the example of FIG. 3C, the number of items of mass spectrum data obtained during the fractionation period T is still smaller, and is 295, 298, . . . .

Regardless of such fluctuations in the number of items of mass spectrum data obtained during the fractionation period T, the data collection unit 61 adds the measurement start point indication information to the first data item in the fractionation period T. Therefore, in the example in Part (b) of FIG. 2, the measurement start point indication information is added to D1, D298, D597, . . . marked with downward-pointing arrows. On the other hand, in the example in Part (c) of FIG. 2, the measurement start point indication information is added to D1, D296, D594, . . . marked with downward-pointing arrows.

Next, characteristic two-dimensional chromatogram creation operation performed by the two-dimensional LC system according to the present embodiment will be described.

When the user gives a command to create a two-dimensional chromatogram via the input unit 8, in response to the command, the two-dimensional chromatogram creation unit 62 reads a series of the specified mass spectrum data together with the measurement start point indication information. The measurement start point indication information marked with downward-pointing arrows in FIG. 2 has been added to the data read out of the data storage unit 7 and the two-dimensional chromatogram creation unit 62 recognizes delimitation of data obtained chronologically between fractionation periods T based on this information.

Also, regarding each item of the mass spectrum data read out, the two-dimensional chromatogram creation unit 62 sums up the values of strength of all the ions. Consequently, for example, from the mass spectrum data D1 over a predetermined mass-to-charge ratio range at a given measurement time point, the total value of strength of all the ions at the given measurement time point can be found. This corresponds to the value of strength at one measurement time point during creation of a total ion chromatogram.

The sum data of the values of strength of all ions calculated in this way are plotted on a graph with the abscissa representing time lapse of separation in the first-dimension column and the ordinate representing the number (cumulative number) of scan measurements, to create a two-dimensional chromatogram, and in so doing, the data is arranged so that items of the sum data of the values of strength of all ions calculated from the mass spectrum data to which the measurement start point indication information has been added will be placed at the top of respective data lists in the ordinate direction. FIG. 3A, FIG. 3B, and FIG. 3C are diagrams showing data arrangements which result when two-dimensional chromatograms are created using the mass spectrum data to which the measurement start point indication information has been added as shown in Parts (a), (b), and (c) of FIG. 2, respectively. It should be noted that to clarify correspondence between FIG. 2 and FIG. 3, even though the data shown in FIG. 3 is the sum data of the values of strength of all ions, the same notation as in FIG. 2 is used in FIG. 3.

In FIG. 3A, the number of data items contained in one line of data arranged in the ordinate direction is 300. On the other hand, in the example of FIG. 3B, the number of data items included in the data count in the first line is 297 and the number of data items contained in the second data line is 299. That is, the number of data items in a line in the ordinate direction of the two-dimensional chromatogram varies due to fluctuations in the number of data items obtained within the fractionation period T during measurement. If the number of scans is the ordinate, missing portions occur on the upper end of the graph due to the fact that the number of data items is not 300 or due to the fact that the number of data items varies from data line to data line. Thus, the missing portions can be filled in by such a process as inserting dummy data or fitting the temporally immediately preceding data. Also, if time rather than the number of scans is conducted as the ordinate, the upper end can be justified by aligned, as appropriate, the vertical length of a rectangular region which represents the signal strength of one data item.

The two-dimensional chromatogram created in the manner described above is displayed on a screen of the display unit 9 via the main control unit 5. Even if the number of data items obtained during measurement varies among fractionation periods T, since a two-dimensional chromatogram practically unaffected by the variation is drawn, the analyst can properly grasp the state of two-dimensional separation of each component contained in the sample.

Although in the embodiment described above, a measurement start point indication signal is added to the first data item in the fractionation period T during data collection and data is arranged using the measurement start point indication signals during creation of a two-dimensional chromatogram, a similar two-dimensional chromatogram can be created as long as delimitation of a fractionation period T can be identified when data is read out.

Thus, instead of adding a measurement start point indication signal to the first data item in each fractionation period T during data collection, the measurement end indication signal may be added to the last data item, which is at the tail of the fractionation period T.

Figure 4:
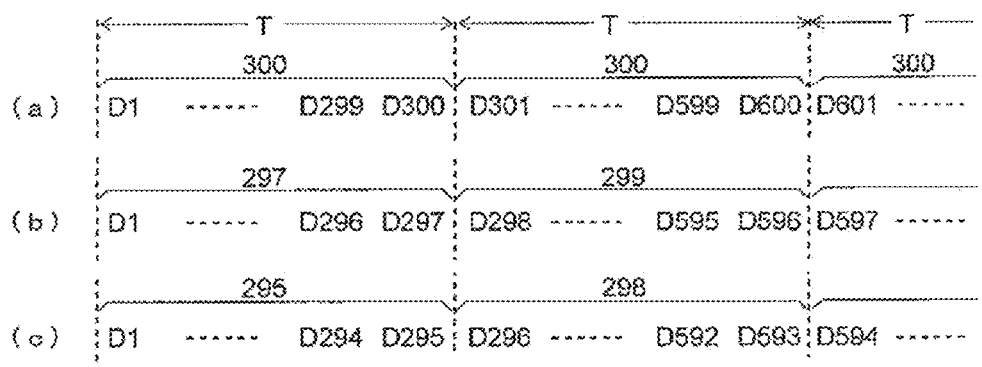
FIG. 4 is an explanatory diagram of data collection operation performed by a two-dimensional LC system according to another embodiment.
Figure 5:
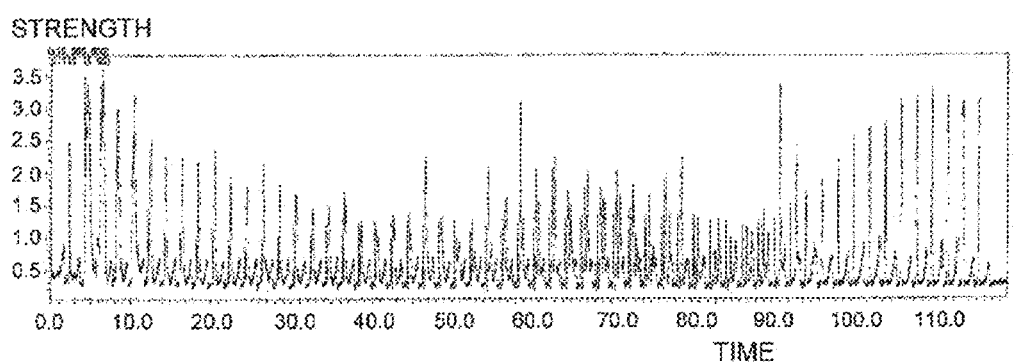
FIG. 5 is a diagram showing an example of a chromatogram based on detection data obtained by a two-dimensional LC system.
Figure 6:
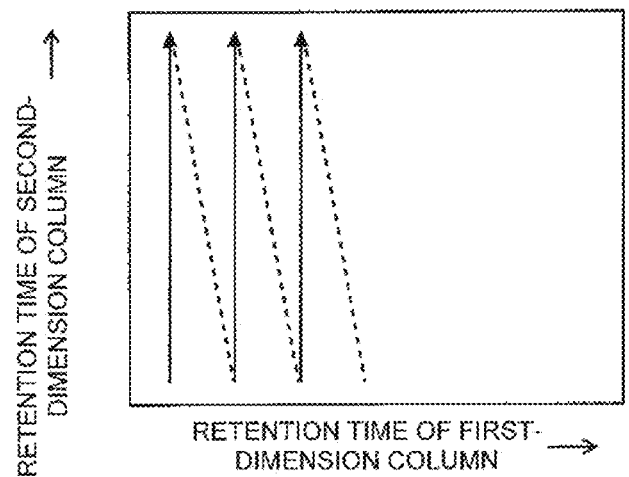
FIG. 6 is a conceptual diagram showing a data arrangement procedure during creation of a two-dimensional chromatogram.
Figure 7:
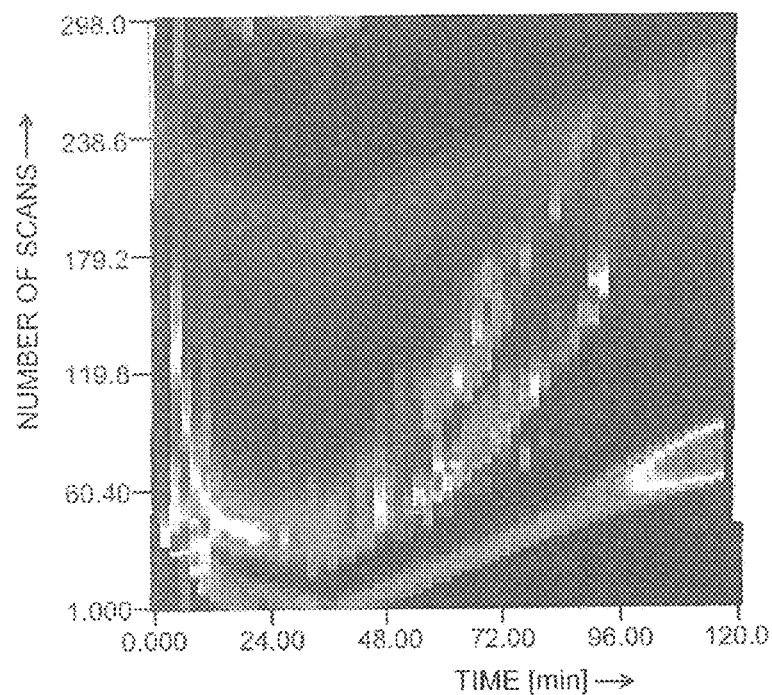
FIG. 7 is a diagram showing an example of a conventional two-dimensional chromatogram.
Figure 8:
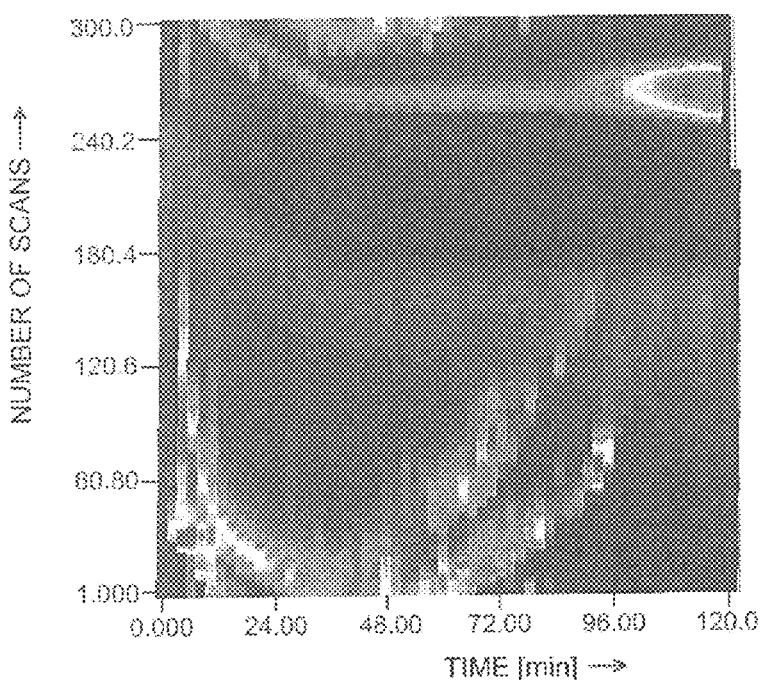
FIG. 8 is a diagram showing an example of a conventional two-dimensional chromatogram.

Also, for each fractionation period T, the number of data items (the number of the scans) contained in the fractionation period T may be determined and recorded together with the data. FIG. 4 is an explanatory diagram of such a data collection operation. For example, in the example shown in Part (b) of FIG. 4, since the numbers of data items obtained in fractionation periods T are 297, 299, . . . in respective fractionation periods T starting from the beginning of measurement, the counts themselves are stored in the data storage unit 7. Then, in creating a two-dimensional chromatogram, delimitation of data among fractionation periods T are recognized based on the counts and the first data item of each fractionation period T is found.

Also, for example, serial numbers may be assigned to scan measurements (or items of the mass spectrum data obtained by the scan measurements) starting from the beginning of measurement and the data number at the start (or at the end) of each fractionation period T may be recorded separately. Alternatively, by recording the time point (elapsed time with respect to the actual time or to an arbitrary time point) of each scan measurement, the first data item of each fractionation period T may be determined based on the time point.

Although the embodiment described above is an example in which the present invention is applied to a two-dimensional LC system, the present invention may be applied to a multi-dimensional GC system (e.g., a comprehensive two-dimensional GC system). Also, it is clear that the present invention can also be applied to a multi-dimensional LC system and multi-dimensional GC system higher than two dimensional. Although the detector is a mass spectrometer in the above embodiment, it is clear that another detector may be used alternatively. For example, a UV/visible spectroscopic detector or photodiode detector may be used as a detector for a multi-dimensional LC system and a TCD, FID, ECD, or FPD may be used as a detector for a multi-dimensional GC system.

Furthermore, the embodiment described above is merely an example of the present invention and it is obvious that in addition to the various variations described above, any change, modification, or addition made as appropriate within the spirit and scope of the present invention is included in the scope of the appended claims.

REFERENCE SIGNS LIST

1 . . . Separation Unit
11, 18 . . . Mobile Phase Container
12, 19 . . . First Pump
13 . . . Injector
14 . . . First-Dimension Column
15 . . . Change-Over Valve
16 . . . Trap Column
17 . . . Second-Dimension Column
2 . . . Mass Spectrometer
3 . . . A/D Converter
4 . . . Analysis Control Unit
5 . . . Main Control Unit
6 . . . Data Processing Unit
61 . . . Data Collection Unit
62 . . . Two-Dimensional Chromatogram Creation Unit
7 . . . Data Storage Unit
8 . . . Input Unit
9 . . . Display Unit

The invention claimed is:

1. A multi-dimensional chromatograph system comprising: an (n-1)th-dimension column, where n is an integer equal to or larger than 2, configured to chronologically separate a plurality of components contained in a sample; a holding unit configured to hold components of the sample, the components being obtained from the (n-1)th-dimension column within a predetermined time period; an nth-dimension column configured to further chronologically separate components of the sample held by the holding unit; and a detection unit configured to detect the components of the sample in sequence, the components being obtained from the nth-dimension column, the multi-dimensional chromatograph system further comprising:

a) data collection means for collecting data items obtained in sequence by the detection unit and recording the data items by adding information to the data items or by associating the information with the data items, the information being capable of identifying data delimitation corresponding to a fractionation of the sample; and b) multi-dimensional chromatogram creation means for determining, based on the information capable of identification, a first data item obtained in relation to the predetermined time period among the data items collected by the data collection means and creating a graph by aligning the data items so as to arrange the first data items of the data items along an axis in a direction of one dimension, wherein the detection unit uses a detector with which a number of data items obtained in relation to the predetermined time period is not constant because a time interval at which detection data is acquired is not constant.

2. The multi-dimensional chromatograph system according to claim 1, wherein the data collection means is configured to record the data obtained in relation to the predetermined time period by adding an identifier to one of the first item and a last item of the data; and the multi-dimensional chromatogram creation means is configured to determine the first item of the data obtained in relation to the predetermined time period, based on the identifier.

3. The multi-dimensional chromatograph system according to claim 1, wherein the data collection means is configured to count and record the number of data items obtained in relation to the predetermined time period at every predetermined time period starting from the beginning of measurement; and the multi-dimensional chromatogram creation means is configured to determine the first item of the data obtained in relation to the predetermined time period, based on the count.

4. The multi-dimensional chromatograph system according to claim 1, wherein the data collection means is configured to record a serial number given to one of the first item and a last item of the data obtained in relation to the predetermined time period, the serial numbers being given according to chronological order of data starting from the beginning of measurement or from a predetermined time point; and the multi-dimensional chromatogram creation means is configured to determine the first item of the data obtained in relation to the predetermined time period, based on the recorded number.

5. The multi-dimensional chromatograph system according to claim 1, wherein the data collection means is configured to record acquisition time of each data item counting from the beginning of measurement or from a predetermined time point; and the multi-dimensional chromatogram creation means is configured to determine the first item of the data obtained in relation to the predetermined time period, based on the recorded acquisition time.

* * * * *